United States Patent
Struble et al.

(10) Patent No.: US 7,181,272 B2
(45) Date of Patent: Feb. 20, 2007

(54) CARDIAC RESTRAINT WITH ELECTRODE ATTACHMENT SITES

(75) Inventors: Chester Struble, Eijsden (NL); Pierre A. Grandjean, Warsage (BE); Volkert A. Zeijlemaker, Landgraaf (NL); Karel F. A. A. Smits, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 287 days.

(21) Appl. No.: 10/126,539

(22) Filed: Apr. 22, 2002

(65) Prior Publication Data
US 2003/0199955 A1  Oct. 23, 2003

(51) Int. Cl.
*A61N 1/05* (2006.01)

(52) U.S. Cl. .............. 607/4; 607/8; 607/119; 607/129; 607/130; 607/149; 600/393; 600/374; 600/386

(58) Field of Classification Search ........... 607/149, 607/119, 129, 130, 8, 5, 148, 152, 4; 600/393, 600/374, 386
See application file for complete search history.

(56) References Cited

U.S. PATENT DOCUMENTS

| | | | | |
|---|---|---|---|---|
| 3,572,345 A | * | 3/1971 | Auphan | 607/129 |
| 3,587,567 A | * | 6/1971 | Schiff | 601/21 |
| 3,612,061 A | * | 10/1971 | Collins et al. | 607/148 |
| 4,030,509 A | * | 6/1977 | Heilman et al. | 607/17 |
| 4,316,472 A | | 2/1982 | Mirowski et al. | |
| 4,375,817 A | | 3/1983 | Engle et al. | |
| 4,381,012 A | * | 4/1983 | Russek | 600/382 |
| 4,384,585 A | | 5/1983 | Zipes | |
| 4,577,633 A | | 3/1986 | Berkovits et al. | |
| 4,587,970 A | | 5/1986 | Holley et al. | |
| 4,628,937 A | * | 12/1986 | Hess et al. | 600/374 |
| 4,726,380 A | | 2/1988 | Vollmann | |
| 4,727,877 A | | 3/1988 | Kallok | |
| 4,800,883 A | | 1/1989 | Winstrom | |
| 4,830,006 A | | 5/1989 | Haluska | |
| 4,880,005 A | | 11/1989 | Pless et al. | |
| 4,925,443 A | * | 5/1990 | Heilman et al. | 600/16 |
| 4,949,719 A | | 8/1990 | Pless et al. | |
| 4,953,551 A | | 9/1990 | Mehra et al. | |
| 5,150,706 A | | 9/1992 | Cox et al. | |
| 5,163,427 A | | 11/1992 | Keimel | |
| 5,179,946 A | * | 1/1993 | Weiss | 607/4 |
| 5,188,105 A | | 2/1993 | Keimel | |
| 5,199,428 A | | 4/1993 | Obel et al. | |
| 5,207,218 A | | 5/1993 | Carpentier et al. | |
| 5,269,298 A | | 12/1993 | Adams et al. | |
| 5,330,507 A | | 7/1994 | Schwartz | |
| 5,331,966 A | | 7/1994 | Bennet et al. | |
| 5,582,580 A | * | 12/1996 | Buckman, Jr. et al. | 601/41 |
| 5,607,385 A | | 3/1997 | Francischelli et al. | |

(Continued)

*Primary Examiner*—Kennedy Schaetzle
(74) *Attorney, Agent, or Firm*—Girma Wolde-Michael; Paul H. McDowall

(57) ABSTRACT

The invention is directed to techniques for electrode placement around a heart. A harness having one or more attachment sites may be secured around the heart, and electrodes may be secured at the attachment sites as desired by the physician for the patient. The electrodes may be, for example, pacing and sensing electrodes, defibrillation electrodes, or any combination thereof. The harness holds the electrodes in place and also impedes the progress of ventricular dilation. The electrodes attached to the harness may be used for any of several purposes, such as cardiac resynchronization, selective defibrillation, measurement of impedance, pacing and cardioversion.

42 Claims, 8 Drawing Sheets

U.S. PATENT DOCUMENTS

| | | |
|---|---|---|
| 5,702,343 A | 12/1997 | Alferess |
| 5,961,440 A | 10/1999 | Schweich, Jr. et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferess |
| 6,081,748 A | 6/2000 | Struble et al. |
| 6,085,754 A | 7/2000 | Alferess et al. |
| 6,155,972 A | 12/2000 | Nauertz et al. |
| 6,169,922 B1 * | 1/2001 | Alferness et al. ............... 607/5 |
| 6,174,279 B1 | 1/2001 | Girard |
| 6,193,648 B1 | 2/2001 | Krueger |
| 6,261,222 B1 | 7/2001 | Schweich, Jr. et al. |
| 6,282,445 B1 * | 8/2001 | Reinhardt et al. ............. 607/3 |
| 6,564,094 B2 * | 5/2003 | Alferness et al. ............... 607/9 |
| 6,625,487 B2 * | 9/2003 | Herleikson ..................... 607/8 |
| 6,633,780 B1 * | 10/2003 | Berger ........................ 607/129 |
| 6,647,292 B1 * | 11/2003 | Bardy et al. ................... 607/5 |

\* cited by examiner

CARDIAC RESTRAINT WITH ELECTRODE ATTACHMENT SITES

FIELD OF THE INVENTION

The invention relates to treatment of heart failure, and more particularly to systems that use electrodes for functions such as sensing, pacing or defibrillation.

BACKGROUND

Many patients that suffer from congestive heart failure (CHF) develop a wide QRS complex resulting from a delayed activation of one of the ventricles in the heart, and inter- and/or intraventricular electro-mechanical dysynchrony. This ventricular "dysynchrony" may be caused by dilation of the heart, which disrupts the conductive pathways and interferes with depolarization sequences. Ventricular dysynchrony may worsen heart failure symptoms.

In a classic case of ventricular dysynchrony, the patient's right ventricle activates first, and the left ventricle activates at a later time. The patient often experiences a reduction in cardiac output because the ventricles begin contraction at significantly different times. The timing imbalance may also cause the patient to experience paradoxical septal motion, mitral regurgitation or decreased ventricular filling time.

Patients having a wide QRS complex or having inter- and/or intraventricular electro-mechanical dysynchrony may receive benefits from an implanted medical device, such as a pacemaker, that paces both ventricles. The implanted medical device senses or paces atrial contractions, waits a predetermined time (or atrioventricular (AV) delay) after each sensed or paced atrial contraction, and then paces both ventricles. The ventricles may be paced simultaneously, or one ventricle may be paced before another. This bi-ventricular pacing is one form of cardiac resynchronization, and it provides many CHF patients with improvements in quality of life, exercise capacity and overall cardiac function.

Generally speaking, cardiac resynchronization refers to pacing therapies applied by implanted medical devices with pacing leads in two or more complementary chambers of the heart. For purposes of the following discussion, the right and left atria are complementary chambers, and the right and left ventricles are complementary chambers. The right and left atria are complementary because they are the upper chambers that receive blood and transfer it to the ventricles. The right and left ventricles are complementary chambers because they receive blood from the atria and pump the blood to the heart. In a heart in a healthy patient, complementary chambers activate at approximately the same time. In a heart in a patient suffering from a condition such as CHF, complementary chambers activate at different times.

In response to a sensed or paced event, the pacemaker delivers pacing pulses or stimulations to two complementary chambers of the heart. The pacing pulses may be, but need not be, delivered simultaneously. Although the discussion that follows emphasizes bi-ventricular pacing to treat ventricular dysynchrony, cardiac resynchronization also encompasses, for example, resynchronization of atrial contractions.

As noted above, ventricular "dysynchrony" may be caused by dilation of the heart. This condition, known as dilated cardiomyopathy (DCM), may progress, causing the dilation to become more pronounced. In a typical case of DCM, left ventricular failure leads to left ventricular dilation, which is followed by right ventricular failure and right ventricular dilation. Single-ventricular failure and bi-ventricular failure are very serious, and may cause death.

Multiple-chamber pacing systems in general, and bi-ventricular and bi-atrial pacing systems in particular, are known in the art. Many of the techniques, however, employ a modest number of electrodes and may be difficult to customize for the needs of a particular patient.

In addition, various jacketing and reinforcing devices are known in the art. These devices constrain expansion of the ventricles and impede the progression of DCM. These devices, however, do not necessarily assist with cardiac resynchronization. In U.S. Pat. No. 6,169,922 to Alferness et al., a cardiac jacket with interwoven electrodes is disclosed, but the versatility of the system is limited and the electrodes are useful for defibrillation rather than for resynchronization. Examples of these techniques and/or devices may be found in the issued U.S. Patents listed in Table 1 below.

TABLE 1

| U.S. Pat. No. | Inventor | Issue Date |
| --- | --- | --- |
| 5,150,706 | Cox et al. | Sep. 29, 1992 |
| 5,607,385 | Francischelli et al. | Mar. 4, 1997 |
| 5,702,343 | Alferness | Dec. 30, 1997 |
| 5,800,528 | Lederman et al. | Sep. 1, 1998 |
| 5,961,440 | Schweich, Jr. et al. | Oct. 5, 1999 |
| 6,045,497 | Schweich, Jr. et al. | Apr. 4, 2000 |
| 6,050,936 | Schweich, Jr. et al. | Sep. 18, 2000 |
| 6,059,715 | Schweich, Jr. et al. | May 9, 2000 |
| 6,076,013 | Brennan et al. | Jun. 13, 2000 |
| 6,077,214 | Mortier et al. | Jun. 20, 2000 |
| 6,077,218 | Alferness | Jun. 20, 2000 |
| 6,081,748 | Struble et al. | Jun. 27, 2000 |
| 6,085,754 | Alferness et al. | Jul. 11, 2000 |
| 6,155,972 | Nauertzetal. | Dec. 5, 2000 |
| 6,169,922 B1 | Alferness et al. | Jan. 2, 2001 |
| 6,174,279 B1 | Girard | Jan. 16, 2001 |
| 6,193,648 B1 | Krueger | Feb. 27, 2001 |
| 6,261,222 B1 | Schweich, Jr. et al. | Jul. 17, 2001 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to multiple-chamber cardiac pacemakers in general, and with cardiac pacemakers that provide cardiac resynchronization or bi-ventricular pacing in particular. These problems include, for example, an inability to adapt a cardiac resynchronization device to the needs of the patient.

The needs of the patient may depend upon factors such as his past medical history and his anatomy. In conventional cardiac resynchronization, sensing and pacing electrodes may by implanted endocardially, that is, within the chambers of the heart, or endovenously, that is, in the cardiac veins. In some patients, such electrode placements are less than ideally effective due to conditions such as myocardial scar tissue created by earlier myocardial infarctions. For such patients, the electrodes may be more effective when placed epicardially, that is, on the surface of the heart. One object of the invention is to make epicardial electrode placement easier and more easily customized to the patient.

Another object of the invention is to allow for more electrode placements than may be possible with endocardial or endovenous implantation. In some patients, cardiac resynchronization may be performed more efficiently when several electrodes are disposed proximate to a single cardiac chamber. When more electrodes are disposed around a chamber, the conductive pathways activating the chamber can be mapped, and strategies for efficient electrical pacing stimulation of the chamber can be developed.

The invention is not limited to placement of electrodes for pacing and/or cardiac resynchronization. It is a further object of the invention to provide for versatile electrode placement that may serve a wide variety of needs. For example, electrodes may be placed at attachment sites to assess cardiac output via measuring impedance between the electrodes. In a patient suffering from CHF, for example, cardiac output is an important quantity that bears upon the efficiency of the heart and the efficacy of treatment such as cardiac resynchronization. The invention is also sufficiently versatile to provide attachment sites for defibrillation electrode arrays that may generate selective defibrillation fields. Selective defibrillation fields may be lifesaving to patients that suffer from ventricular tachycardia or ventricular fibrillation.

Because many of the patients who need cardiac resynchronization suffer from DCM, a further object of the invention is to restrain the heart and prevent further dilation. The techniques of the invention therefore address the patient's condition and prevent the condition from worsening.

Various embodiments of the invention may possess one or more features capable of fulfilling the above objects. In general, the invention includes a harness that restrains the heart and impedes the progression of DCM. The harness further includes attachment sites for electrodes. The electrodes may be attached to an implanted medical device such as a pacemaker, a resynchronizer, a pacemaker-cardioverter-defibrillator or a cardiac monitor. The electrodes may be used for sensing electrical activity of the heart, delivering pacing pulses to the heart, or defibrillating the heart. Because the harness includes a plurality of attachment sites, a physician may attach electrodes to those sites on the heart that will be most beneficial for the patient. The harness holds the electrodes in place.

The invention may have one or more advantages. By affixing electrodes to the harness, the physician can customize electrode placement to the unique anatomy of the patient. In addition, the physician may place more electrodes, and could place those electrodes at more sites, than could be done by conventional endocardial placement. Further, the harness that assists electrode placement also serves to retard the progression of DCM.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

In the following detailed description of the preferred embodiments, reference is made to the accompanying drawings that form a part hereof, and in which are shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
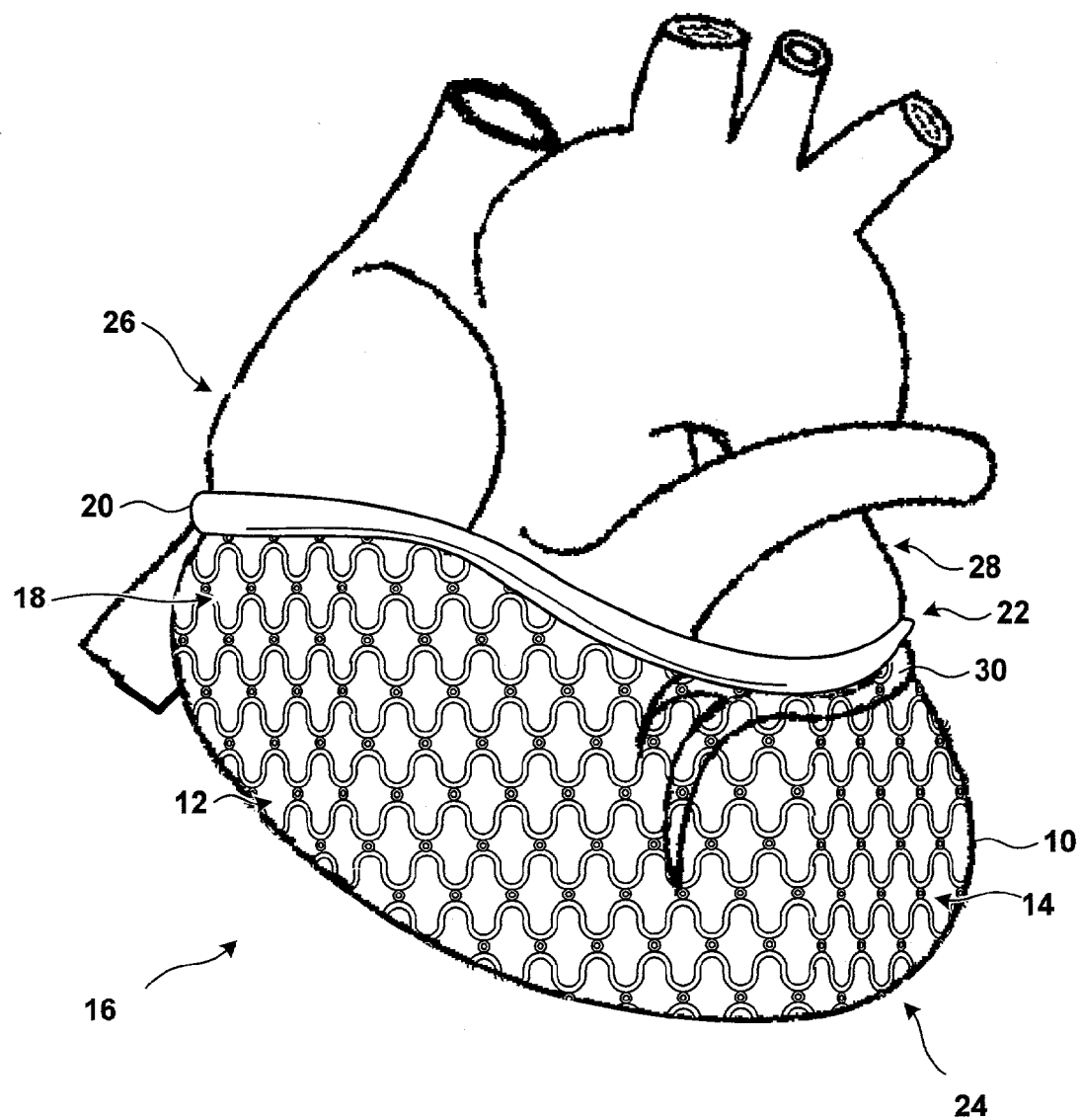
FIG. 1 shows a human heart with an exemplary harness.

FIG. 1 shows a human heart 10. Right ventricle 12 and left ventricle 14 of heart 10 are jacketed by a harness 16. Harness 16 includes a mesh-like restraint 18 and a circumferential attachment member 20. Circumferential attachment member 20 secures harness 16 proximate to the base 22 of heart 10.

Harness 16 may be placed around heart 10 during open-heart surgery. The patient is typically placed in the supine position and the physician performs a median sternotomy, incising and opening the patient's chest. Thereafter, the physician may employ a rib-spreader to spread the rib cage apart and obtain access to heart 10.

Harness 16 may be deployed using any of a number of techniques. Harness 16 may be deployed by unrolling harness 16 over the apex 24, much like a stocking is unrolled over a foot. Another technique may be to slip heart 10 into a loose harness 16, and tighten harness 16 using a drawstring, a suture, a strap, a clasp or other tightening apparatus (not shown in FIG. 1).

The dimensions of harness 16 shown in FIG. 1 are exemplary and the invention is not limited to the embodiment shown. In particular, harness 16 is deployed so that right atrium 26 and left atrium 28 are largely unconfined by harness 16, but right ventricle 12 and left ventricle 14 are largely confined. Various embodiments of harness 16 may extend to confine more of atria 26, 28, or may extend to confine less of ventricles 12, 14.

Mesh-like restraint 18 may be generally composed of biocompatible material such as silicone polymers. Restraint 18 may be generally flexible, but may have limited flexibility in tension. The flexibility allows restraint 18 to conform to the shape of heart 10 as heart 10 beats and further allows heart 10 to perform normal functions. In particular, when harness 16 is in place, heart 10 can receive blood, fill, contract and relax properly. In addition, internal valves (not shown) can open and close properly, and coronary perfusion through coronary vessels 30 is unimpeded.

The flexibility of restraint 18 may be limited, however. Although restraint 18 may be loose enough to permit proper cardiac function, restraint 18 may be tight enough to limit ventricular expansion. One form of harmful expansion is ventricular dilation. Restraint 18 limits ventricular dilation, thereby impeding the progression of DCM. In addition, harness 16 may also provide support to weak areas of heart 10, such as regions of heart 10 that may have been weakened by infarction or regions of heart 10 that may be susceptible to aneurysm.

Figure 2:
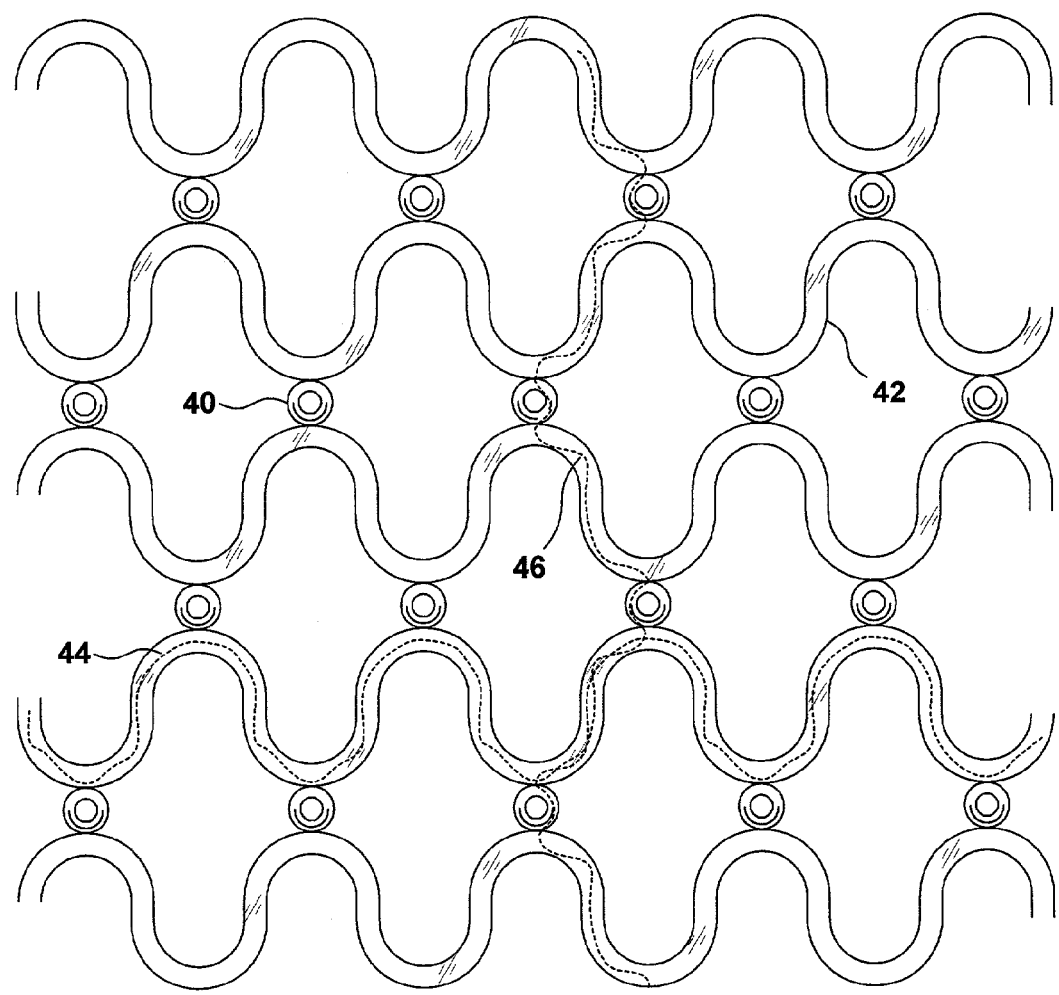
FIG. 2 is a plan view of an exemplary restraint of the harness shown in FIG. 1.

Mesh-like restraint 18 includes a plurality of attachment sites for attachment of devices such as electrodes and electrode arrays. FIG. 2 is a detailed view of exemplary restraint 18 shown in FIG. 1. In the example of FIG. 2, restraint 18 includes a plurality of O-rings 40. As will be described below, O-rings 40 serve as attachment sites for electrodes or other sensors. Restraint 18 further includes a plurality of lattice members 42. Lattice members 42 provide the basic structure of restraint 18 and are generally also the members that are the most flexible. When restraint 18 stretches to accommodate the motion of heart 10, it is principally lattice members 42 that stretch.

The shape of lattice members 42 may contribute to the degree of stretch of lattice members 42. In exemplary restraint 18 shown in FIG. 2, lattice members 42 have an approximately sinusoidal shape that extends further in the longitudinal direction than in the latitudinal direction. Accordingly, lattice members 42 may accommodate more latitudinal stretching and less longitudinal stretching.

O-rings 40 may be flexible as well. Because O-rings 40 may be small relative to lattice members 42, O-rings 40 may contribute to latitudinal and longitudinal stretching of restraint 18 to a small degree. The flexibility of O-rings 40 may be important, however, in that O-rings may deform to couple to devices such as electrode assemblies, as will be shown below.

Restraint 18 may be molded with a single piece of biocompatible material, or woven or otherwise constructed from multiple pieces of biocompatible material. In addition, restraint 18 may include one or more reinforcing members such as threads or wires to limit expansion of restraint 18 under tension. FIG. 2 shows an exemplary latitudinal reinforcing member 44 and an exemplary longitudinal reinforcing member 46. Reinforcing members may be molded inside the biocompatible material that forms restraint 18.

In the embodiment shown in FIG. 2, O-rings 40 couple lattice members 42 to one another. In other words, the attachment sites may provide structural integrity to harness 16. The invention also encompasses embodiments in which the attachment sites provide little or no structural integrity, such as embodiments in which lattice members 42 are coupled to one another directly and O-rings 40 are coupled to lattice members 42, but do not couple lattice members 42 to one another.

Figure 3:
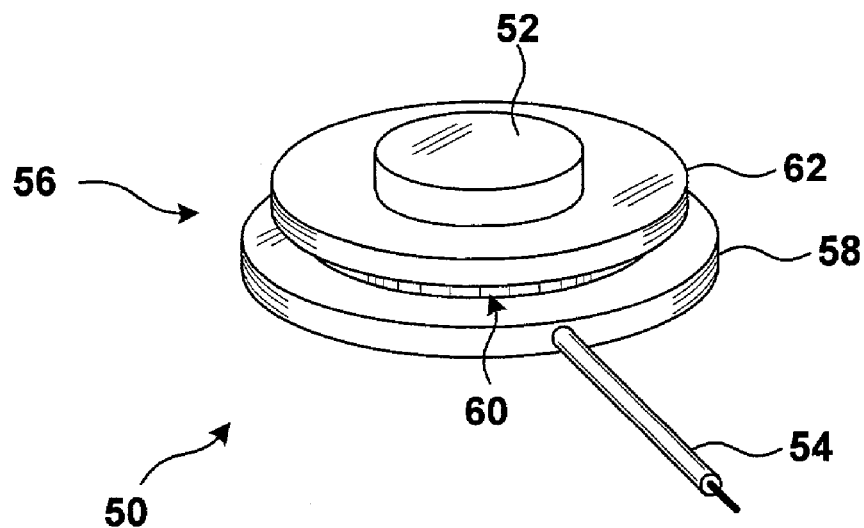
FIG. 3 is a perspective view of an exemplary electrode device that may be affixed to the exemplary harness shown in FIG. 1.

FIG. 3 shows an exemplary device that may be coupled to a restraint such as restraint 18. Electrode assembly 50 may be coupled to any harness that includes an O-ring attachment site sized to receive electrode assembly 50. In addition, electrode assembly 50 may be coupled to attachment sites of other shapes as well.

Electrode assembly 50 includes electrode 52, which may be electrically coupled to lead 54. Electrode assembly 50 also includes housing 56. Housing 56 comprises a base 58, an inner disc 60 and an outer disc 62. Base 58, inner disc 60 and outer disc 62 may be formed from thermoplastic such as polycarbonate, ABS, polysulfone, polyester and polyurethane, and including rigid and semi-rigid elastomers such as silicone rubber, natural rubber, synthetic rubber, and polyurethane. Base 58, inner disc 60 and outer disc 62 may be formed from a single piece of material. In some embodiments, however, outer disc 62 may deform to couple electrode assembly 50 to an attachment site on harness 16, and accordingly outer disc 62 may be formed from a more flexible material than base 58 and inner disc 60.

Figure 4:
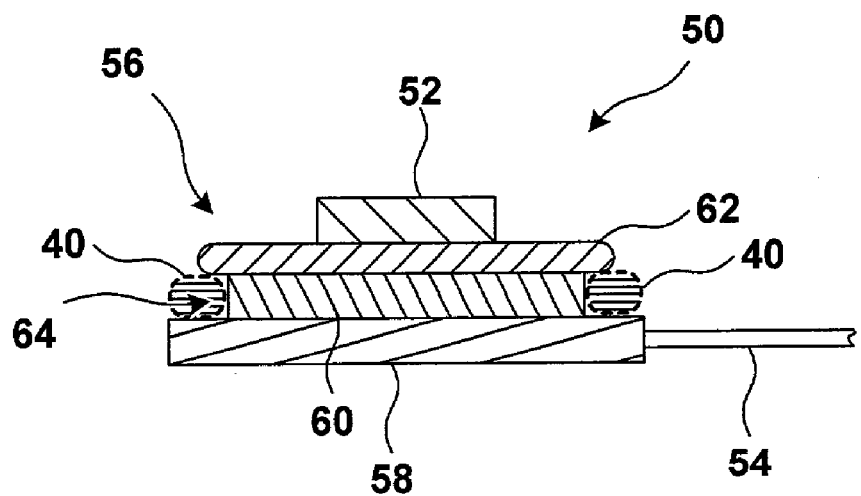
FIG. 4 is a cross-sectional side view of the exemplary electrode device of FIG. 3, showing engagement between the electrode device and an O-ring of the exemplary harness shown in FIG. 1.

FIG. 4 is a cutaway view of electrode assembly 50 coupled to an attachment site such as an O-ring 40. Base 58, inner disc 60 and outer disc 62 form a groove 64 that receives O-ring 40. When electrode assembly 50 is pressed against an attachment site, O-ring 40 deforms to extend around outer disc 62, or outer disc 62 flexes to allow O-ring 40 to pass around outer disc 62, or both. When O-ring 40 passes outer disc 62, O-ring 40 snaps into groove 64.

A physician may attach electrode assembly 50 to an attachment site prior to or during surgery. In either case, the physician positions electrode assembly 50 proximate to the attachment site and pushes them together. In the exemplary embodiment shown in FIG. 4, electrode assembly 50 securely snap couples to the attachment site, with no separate fastener or adhesive.

Figure 5:
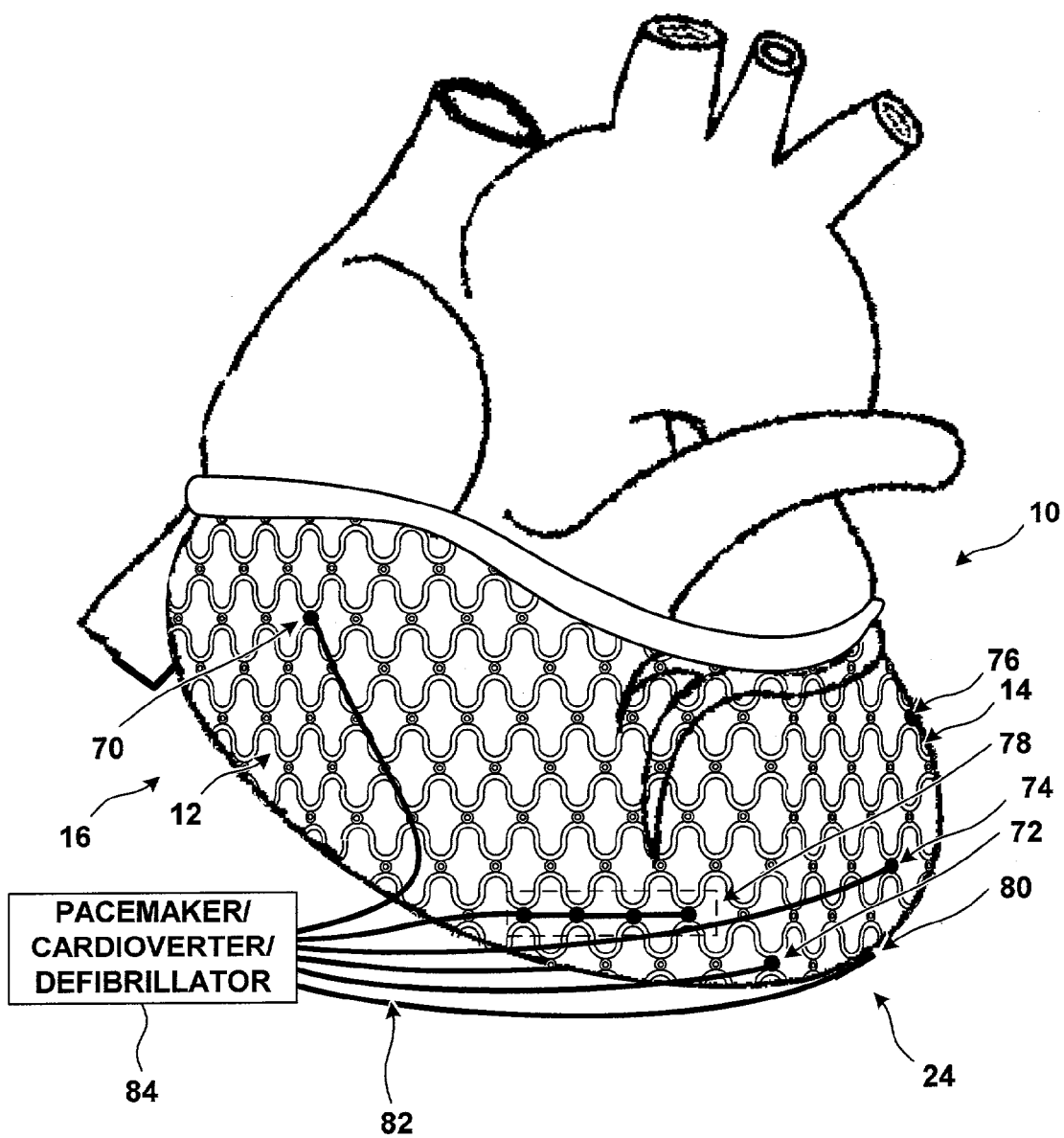
FIG. 5 is a schematic of a human heart with an exemplary harness and several affixed electrodes, in conjunction with an implanted medical device.

FIG. 5 shows heart 10 with harness 16, and several electrodes coupled to harness 16. The electrode placements are merely exemplary, and the invention is not limited to the placements shown. Indeed, an advantage of the invention is that the invention makes possible a virtually unlimited number of configurations of electrodes.

In the exemplary configuration shown in FIG. 5, the physician has placed two right ventricular electrodes 70, 72, and two left ventricular electrodes 74, 76. Right and left ventricular electrodes 70, 72, 74, 76 may serve as pacing and sensing electrodes, sensing electrical signals attendant to the depolarization and repolarization of heart 10, and providing pacing pulses for causing depolarization of proximate cardiac tissue. In addition, the physician has placed a defibrillation electrode array 78 proximate to right ventricle 12 and an indifferent electrode 80 near the apex 24. Indifferent electrode 80 may be a common anode with respect to other electrodes 70, 72, 74, 76, 78.

Electrodes 70, 72, 74, 76, 78 are coupled by leads 82 to an implantable medical device (IMD) 84 such as a pacemaker, a resynchronizer, a pacemaker-cardioverter-defribrillator or a cardiac monitor. IMD 84 receives signals detected by electrodes 70, 72, 74, 76, delivers pacing pulses via electrodes 70, 72, 74, 76, and delivers defibrillation pulses via electrode array 78.

Figure 6:
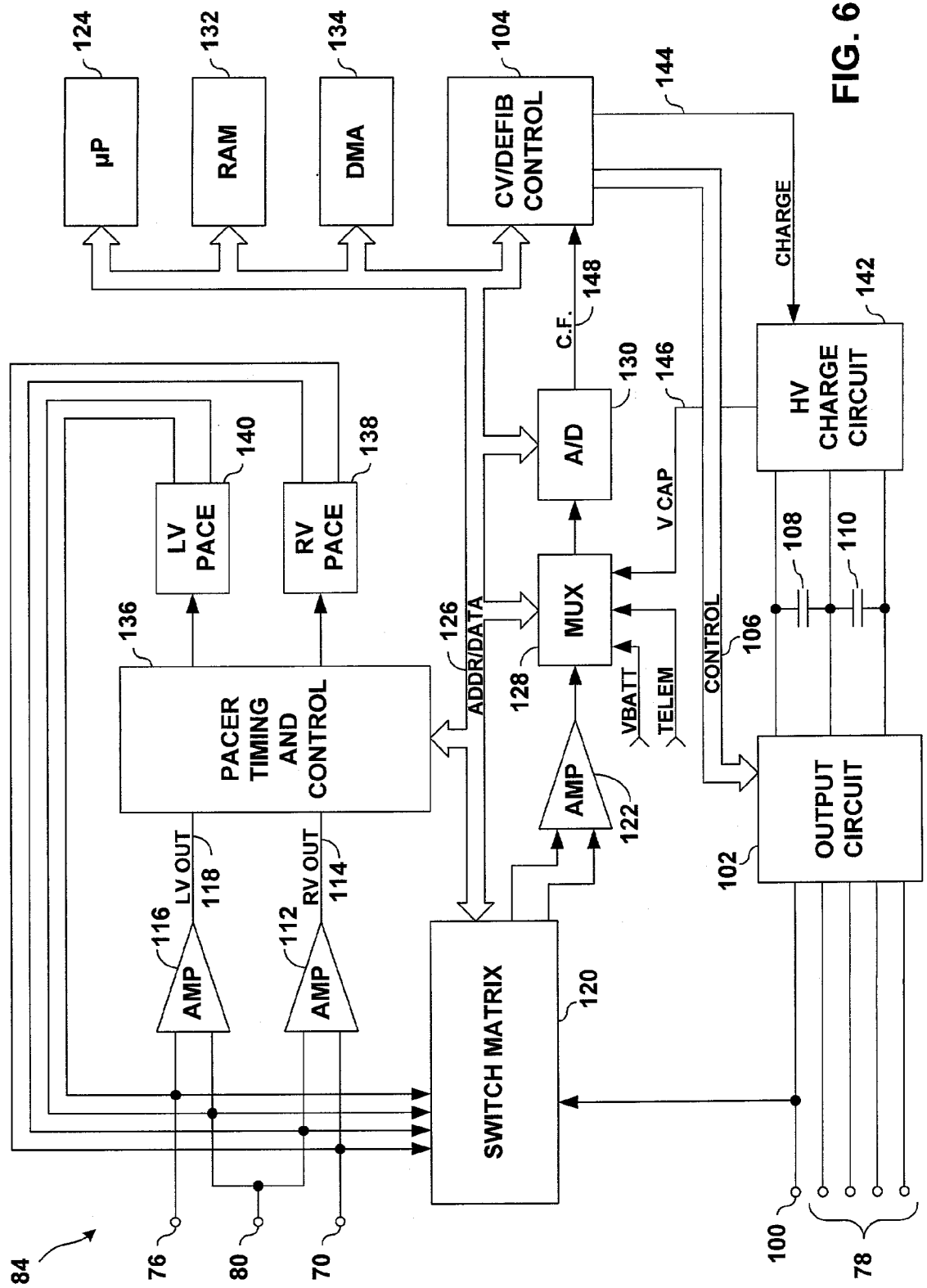
FIG. 6 is a functional schematic diagram of an embodiment of an implantable medical device shown in FIG. 5.

FIG. 6 is a functional schematic diagram of one embodiment of IMD 84 of the present invention. This diagram should be taken as exemplary of the type of device in which various embodiments of the present invention may be embodied, and not as limiting, as it is believed that the invention may be practiced in a wide variety of device implementations, including pacemakers that do no provide cardioversion or defibrillation therapies, and cardioverters and defibrillators which do not provide anti-tachycardia pacing therapies.

IMD 84 is provided with an electrode system. If the electrode configuration of FIG. 5 is employed, electrode 80 is common to right ventricular electrode 70 and left ventricular electrode 76. IMD 84 is not limited to the electrodes shown. In particular, IMD 84 may be modified to include ventricular electrodes 72 and 76, as well as atrial electrodes (not shown in FIGS. 1–5) that may be used to sense P-waves and pace the atria.

Electrode 100 in FIG. 6 may include the uninsulated portion of a housing of IMD 84, or may be common electrode 80. Defibrillation electrode array 78 is coupled to high voltage output circuit 102, which includes high voltage switches controlled by CV/defib control logic 104 via control bus 106. Switches disposed within circuit 102 determine which electrodes are employed and which electrodes are coupled to the positive and negative terminals of a capacitor bank (which includes capacitors 108 and 110) during delivery of defibrillation pulses. When more than one defibrillation electrode array 78 is coupled to high voltage output circuit 102, as will be described below in connection with FIGS. 8 through 13, high voltage output circuit 102, under the control of CV/defib control logic 104, determines which electrode arrays are employed and which electrode arrays are coupled to the positive and negative terminals of a capacitor bank (including capacitors 108 and 110) during delivery of defibrillation pulses.

Electrode 70 is located proximate to right ventricle 12 of the patient and is coupled to the R-wave amplifier 112, which preferably takes the form of an automatic gain controlled amplifier providing an adjustable sensing threshold as a function of the measured R-wave amplitude. A signal is generated on R-out line 114 whenever the signal sensed between electrodes 70 and 80 exceeds the present sensing threshold.

Similarly, electrode 76 is located proximate to left ventricle 14 of the patient and is coupled to the R-wave amplifier 116, which preferably also takes the form of an automatic gain controlled amplifier providing an adjustable sensing threshold as a function of the measured R-wave amplitude. A signal is generated on R-out line 118 whenever the signal sensed between electrodes 76 and 80 exceeds the present sensing threshold. The general operation of R-wave amplifiers 112, 116 may correspond to that disclosed in U.S. Pat. No. 5,117,824 to Keimel et al., hereby incorporated by reference herein in its entirety.

Switch matrix 120 is used to select which of the available electrodes are coupled to wide band (0.5–200 Hz) amplifier 122 for use in digital signal analysis. Selection of electrodes is controlled by microprocessor 124 via data/address bus 126, which selections may be varied as desired. Signals from the electrodes selected for coupling to bandpass amplifier 122 are provided to multiplexer 128, and thereafter converted to multi-bit digital signals by A/D converter 130, for storage in random access memory 132 under control of direct memory access circuit 134. Microprocessor 124 may employ digital signal analysis techniques to characterize the digitized signals stored in random access memory 132 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 136 preferably includes programmable digital counters which control the basic time intervals associated with DDD, VVI, DVI, VDD, AAI, DDI and other modes of single and multi-chamber pacing well known to the art. Circuitry 136 also preferably controls escape intervals associated with anti-tachyarrhythmia pacing in both the atrium and the ventricle, employing any anti-tachyarrhythmia pacing therapies known to the art.

Intervals defined by pacing circuitry 136 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 124, in response to stored data in memory 132 and are communicated to pacing circuitry 136 via address/data bus 126. Pacer circuitry 136 also determines the amplitude of the cardiac pacing pulses under control of microprocessor 124.

During pacing, escape interval counters within pacer timing/control circuitry 136 are reset upon sensing of R-waves as indicated by a signals on lines 114 and 118 and in accordance with the selected mode of pacing on time-out trigger generation of pacing pulses by pacer output circuitry 138 and 140, which are coupled to electrodes 70, 76 and 80. Escape interval counters are also reset on generation of pacing pulses and thereby control the basic timing of cardiac pacing functions, including anti-tachyarrhythmia pacing. The durations of the intervals defined by escape interval timers are determined by microprocessor 124 via data/address bus 126. The value of the count present in the escape interval counters when reset by sensed R-waves may be used to measure the durations of intervals such as R—R intervals, which measurements are stored in memory 132 and used to detect the presence of tachyarrhythmias.

Microprocessor 124 most preferably operates as an interrupt driven device, and is responsive to interrupts from pacer timing/control circuitry 136 corresponding to the occurrence of sensed R-waves and corresponding to the generation of cardiac pacing pulses. Those interrupts are provided via data/address bus 126. Any necessary mathematical calculations to be performed by microprocessor 124 and any updating of the values or intervals controlled by pacer timing/control circuitry 136 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No.

WO92/8198, by Adams et al., and in the article "Automatic Tachycardia Recognition," by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 124 into the pacer timing and control circuitry 136, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 124 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 124 activates cardioversion/defibrillation control circuitry 104, which initiates charging of high voltage capacitors 108 and 110 via charging circuit 142, under the control of high voltage charging control line 144. The voltage on the high voltage capacitors is monitored via VCAP line 146, which is passed through multiplexer 128 and in response to reaching a predetermined value set by microprocessor 124, results in generation of a logic signal on Cap Full (CF) line 148 to terminate charging. Thereafter, timing of the delivery of the defibrillation or cardioversion pulse is controlled by pacer timing/control circuitry 136. Following delivery of the fibrillation or tachycardia therapy microprocessor 124 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing fluctions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 6, delivery of cardioversion or defibrillation pulses is accomplished by output circuit 102 under the control of control circuitry 104 via control bus 106. Output circuit 102 determines whether a monophasic or biphasic pulse is delivered, the polarity of the electrodes and which electrodes are involved in delivery of the pulse. Output circuit 102 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above-cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 84 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 7:
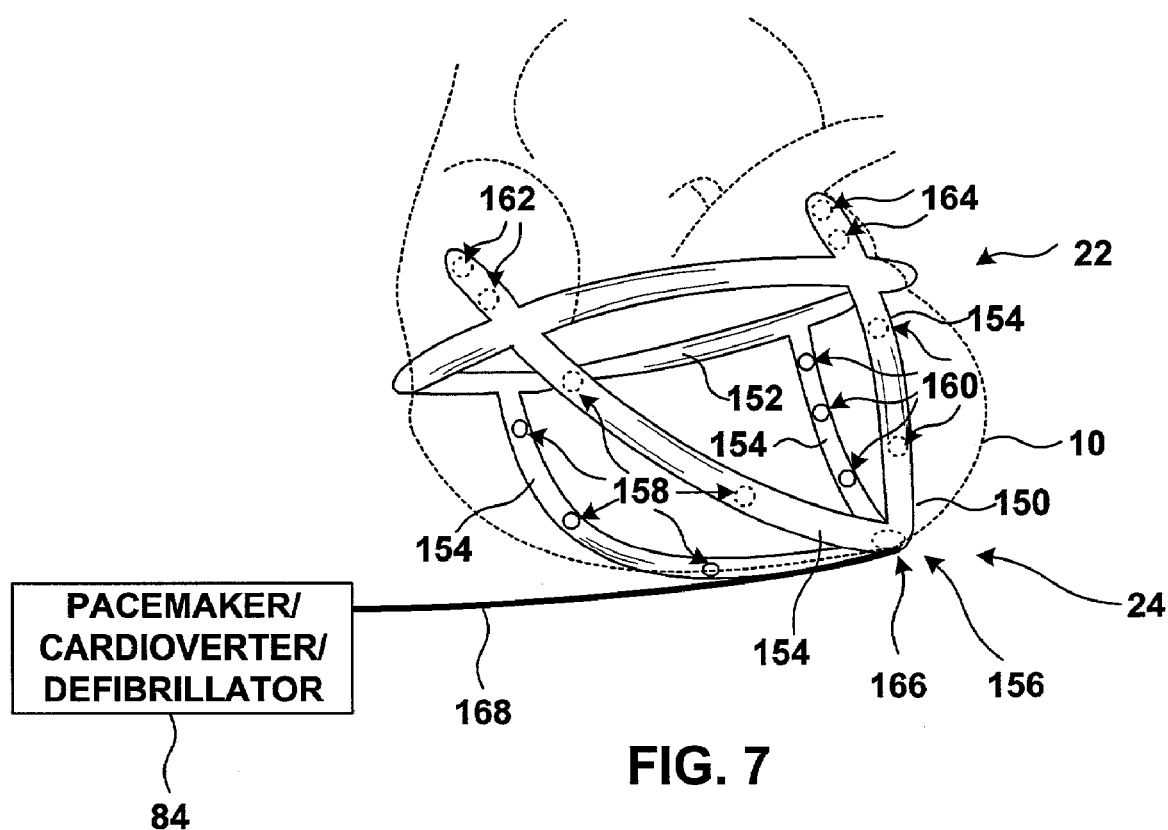
FIG. 7 is a schematic of a human heart with another exemplary harness and several affixed electrodes, in conjunction with an implanted pacemaker.

FIG. 7 shows an alternate embodiment of a harness 150, shown in conjunction with an outline of a human heart 10. Harness 150 includes a circumferential attachment member 152 that secures harness 150 proximate to the base 22 of heart 10. The embodiment of harness 150 shown in FIG. 7 includes four support members 154 that are coupled to circumferential attachment member 152 and descend to join at a junction 156 near apex 24. The invention is not limited to four support members 154, but may include more or fewer support members 154. Support members 154 and circumferential attachment member 152 cooperate to act like a girdle, limiting ventricular dilation and impeding the progression of DCM.

Harness 150 may be placed around heart 10 using techniques similar to those described above in connection with harness 16. During open-heart surgery, harness 150 may be deployed by unrolling, for example, or by slipping loose harness 150 around heart 10, then tightening harness 150 with a tightening apparatus (not shown in FIG. 7).

Support members 154 and circumferential attachment member 152 may further supply attachment sites 158, 160, 162, 164 for electrodes. In particular, harness 150 may include one or more right ventricular electrode attachment sites 158 and/or one or more left ventricular electrode attachment sites 160. The ventricular attachment sites may support multipolar electrodes such as bipolar electrodes, or may support electrodes that share a common indifferent electrode 166 disposed near apex 24.

The invention is not limited to the particular attachment sites shown. Nor is the invention limited to electrodes that pace and sense, but may include defibrillation electrodes as well. In an exemplary application of harness 150, ventricular electrodes may be placed proximate to one or more of the following sites: the right ventricle outflow tractus in the inter-ventricular groove, the right ventricle septum/apex in the inter-ventricular groove, the right ventricular lateral wall proximate to the base, the right ventricular lateral wall proximate to the apex, the left ventricular lateral wall proximate to the base, the left ventricular lateral wall proximate to the apex, the left ventricular lateral wall midway from the base and apex, the left ventricular anterior wall proximate to the base, and the left ventricular anterior wall proximate to the apex. Electrodes may be placed proximate to other ventricular sites as well.

Further, harness 150 may include an attachment site for right atrial electrodes 162 and an attachment site for left atrial electrodes 164. The atrial electrode attachment sites may support bipolar electrodes, and need not use indifferent electrode 166.

Electrical connections for all attachment sites may be embedded within support members 154 and circumferential attachment member 152. Electrical connections may be bundled into a single lead 168 that couples harness 150 to IMD 84. In another variation, a switch matrix similar to switch matrix 120 in FIG. 6 may be built into harness 150, whereby connections between IMD 84 and electrodes at various attachment sites may be established.

When electrical connections are embedded within support members 154 and/or circumferential attachment member 152, electrodes need not have dedicated leads, as shown in FIGS. 3 and 4. Instead, electrodes may be coupled to attachment sites 158, 160, 162, 164 by, for example, insertion of electrode plugs into attachment site receptacles or jacks. The engagement of plug and receptacle holds each electrodes secure and establish the electrical circuit between the electrode and IMD 84. Unused attachment sites may be filled with plugs made of biocompatible and nonconductive material.

Harness 150 may be constructed from any of several biocompatible materials such as silicone polymers. Harness 150 is generally flexible, but has limited flexibility in tension. The flexibility allows harness 150 to conform to the shape of heart 10 as heart 10 beats and further allows heart 10 to perform normal functions.

There are many applications for the invention. As noted above, the invention may be useful for patients needing pacing, cardioversion or defibrillation. The invention is not limited to those applications, however, and may be used for many other purposes.

The invention is useful, for example, in cardiac resynchronization. Ventricles 12, 14 may be paced to improve the hemodynamic efficiency of heart 10. Devices such as harness 16 or harness 150 give the physician many choices for electrode placement that can sense and correct ventricular dysynchrony. In particular, devices such as harness 16 or harness 150 give the physician several options for interventricular cardiac resynchronization, i.e., pacing one ventricle with respect to the other, to improve synchrony between right ventricle 12 and left ventricle 14. Devices such as harness 16 or harness 150 also give the physician several options for intraventricular cardiac resynchronization, i.e., delivering a plurality of pacing pulses to a single ventricle to improve the performance of that ventricle.

By delivering pacing pulses with electrodes at particular attachment sites, for example, an implanted medical device can cause the ventricles to beat with improved efficiency, improving stroke volume and cardiac output. Electrodes at particular attachment sites may also be useful in mapping the electrical activity of heart 10 and developing a pacing strategy that best meets the needs of the patient. In addition, devices such as harness 16 or harness 150 retard the progress of ventricular dilation, which may contribute to the ventricular dysynchrony.

Figure 8:
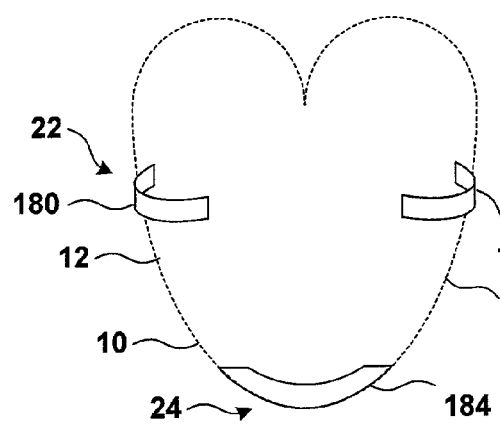
FIG. 8 is a symbolic representation of a heart with three defibrillation electrodes.

Another application for the invention may be selective defibrillation strategies. FIG. 8 shows a configuration of defibrillation electrodes 180, 182, 184 in which different defibrillation strategies may be practiced. Defibrillation electrode 180 is located near the base 22 of heart 10 proximate to right ventricle 12, defibrillation electrode 182 is located near the base 22 of heart 10 proximate to left ventricle 14, and defibrillation electrode 184 is located near the apex 24 of heart 10. The configuration of defibrillation electrodes 180, 182, 184 shown in FIG. 8 may be epicardially placed at the respective sites with a harness such as harness 16 or harness 150. For purpose of illustration of the application, no harness is shown in FIG. 8 or in subsequent figures. Defibrillation electrodes 180, 182, 184 may be similar to defibrillation electrode array 78 shown in FIG. 5.

Figure 9:
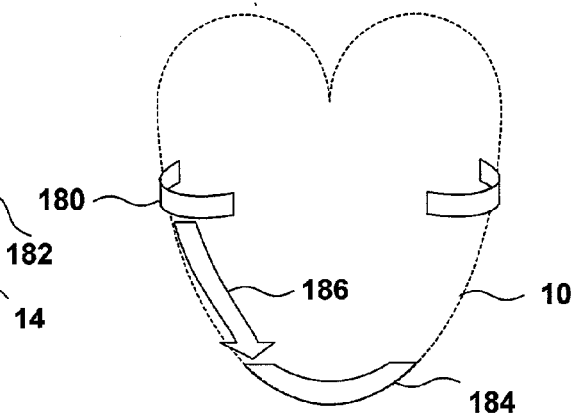
FIGS. 9 through 13 are illustrations of alternative defibrillation techniques that may be implemented using defibrillation electrodes such as those shown in FIG. 8.
Figure 10:
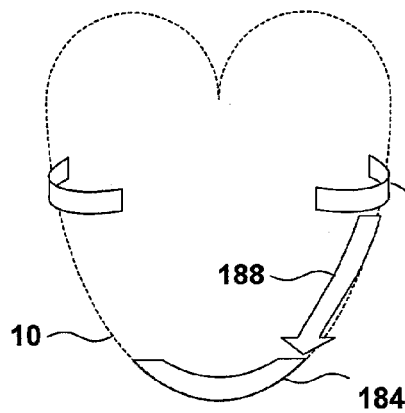
Figure 11:
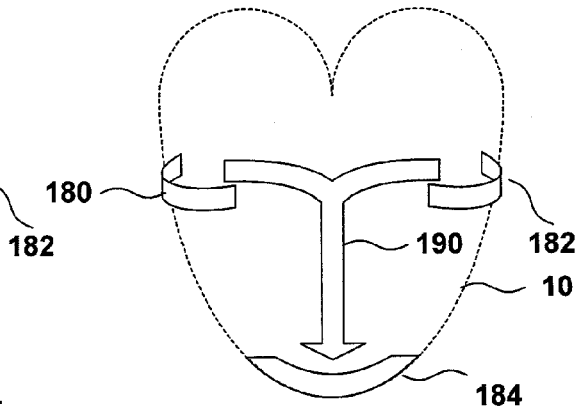

FIGS. 9 through 13 illustrate some possible defibrillation strategies that may be implemented with defibrillation electrodes 180, 182, 184 placed as shown in FIG. 8. In FIG. 9, a defibrillation pulse 186 is sent from right ventricular coil 180 to apical coil 184. Apical coil 184 functions as an indifferent electrode. In FIG. 10, a defibrillation pulse 188 is sent from left ventricular coil 182 to apical coil 184. In this scenario, apical coil 184 functions as an indifferent electrode. In FIG. 11, a defibrillation pulse 190 is sent from right ventricular coil 180 and left ventricular coil 182 to apical coil 184. In this scenario, apical coil 184 functions as an indifferent electrode once again.

Figure 12:
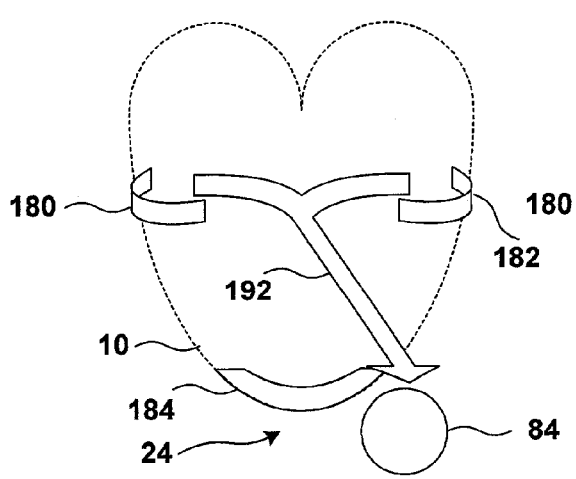
Figure 13:
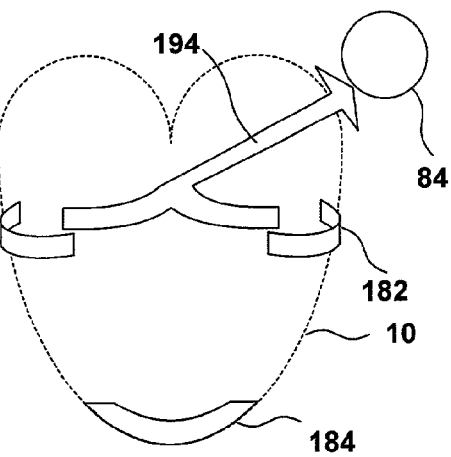

As shown in FIGS. 12 and 13, defibrillation electrodes 180, 182, 184 may be used in conjunction with IMD 84. In particular, the uninsulated portion of a housing of IMD 84 acts as an indifferent electrode. When IMD 84 is implanted below apex 24, such as in an abdominal pocket, a defibrillation pulse 192 may be sent from right ventricular coil 180 and left ventricular coil 182 to IMD 84, as shown in FIG. 12. When IMD 84 is implanted in a pectoral pocket, a defibrillation pulse 194 may be sent from right ventricular coil 180 and left ventricular coil 182 to IMD 84, as shown in FIG. 13.

The defibrillation strategies depicted in FIGS. 9 through 13 are not the only possible strategies. FIGS. 9 through 13 show monophasic pulses, but the strategies may include biphasic pulses as well. Moreover, defibrillation electrodes may be placed at other attachment sites, providing a virtually unlimited number of possibilities for directing energy across the heart 10 of a patient.

The techniques shown in FIGS. 9 through 13 may be used to terminate conditions such as ventricular tachycardia and ventricular fibrillation. In some embodiments, different techniques may be used to terminate the conditions, and the response of the patient to each technique may be observed. Moreover, the placement of defibrillation electrodes at multiple attachment sites allows for different therapies, and perhaps progressively more aggressive therapies, to be employed by IMD 84.

Figure 14:
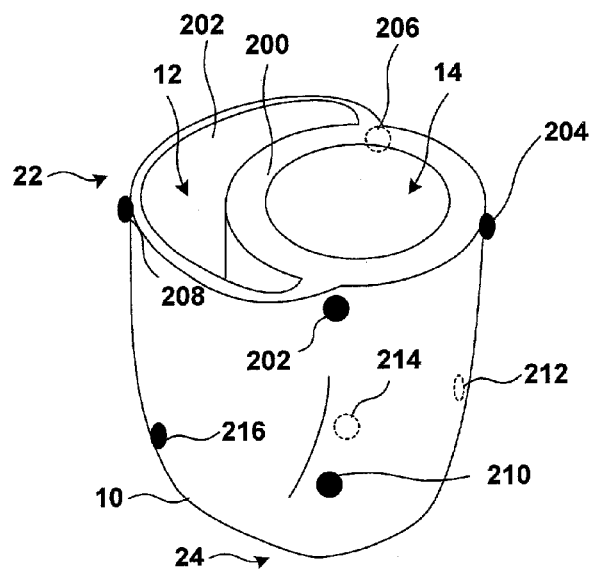
FIG. 14 is a cutaway view of a human heart below the base, showing the right and left ventricles.

A further application for the invention may be measurement of cardiac output. FIG. 14 shows the lower portion of heart 10, cut away near base 22. Right ventricle 12 and left ventricle 14 are separated by the interventricular septum 200.

A configuration of electrodes 202, 204, 206, 208, 210, 212, 214 and 216 has been placed at various sites proximate to ventricles 12, 14. Electrodes 202, 204, 206, 208, 210, 212, 214 and 216 are held in place by a harness such as harness 16 or harness 150, but for purposes of illustration of the application, no harness is shown in FIG. 14 or subsequent figures.

Electrodes 202, 204, 206 and 208 are placed proximate to base 22. Electrode 202 is placed in an anterior position, electrode 204 is placed proximate to left ventricle 14, electrode 206 is placed in a posterior position, and electrode 208 is placed proximate to right ventricle 12. In similar fashion, electrodes 210, 212, 214 and 216 are placed proximate to apex 24. Electrode 210 is placed in an anterior position, electrode 212 is placed proximate to left ventricle 14, electrode 214 is placed in a posterior position, and electrode 216 is placed proximate to right ventricle 12.

In this application, devices such as harness 16 or harness 150 give the physician many choices for electrode placement. The positions of electrodes 202, 204, 206, 208, 210, 212, 214 and 216 are exemplary and the invention is not limited to the positions shown.

By injection of an amount of current into the cardiac tissue via an electrode and by measuring the voltage potential between two electrodes, the impedance between the electrodes can be measured. In general, the impedance measured across a chamber of heart 10 is proportional to the volume of heart 10 and its blood content.

Figure 15:
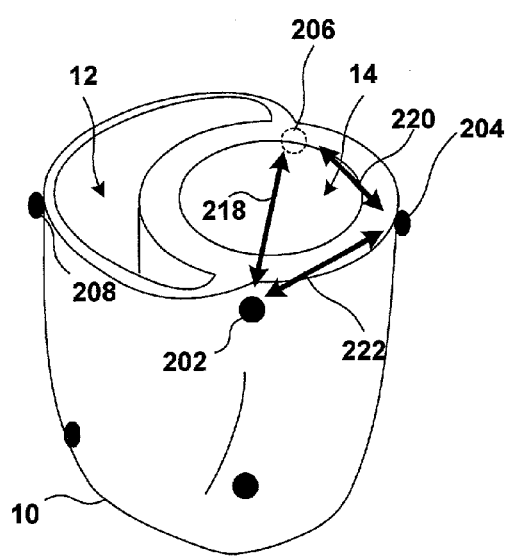
FIGS. 15 through 17 are illustrations of alternative impedance measuring techniques that may be implemented using electrodes such as those shown in FIG. 14.
Figure 16:
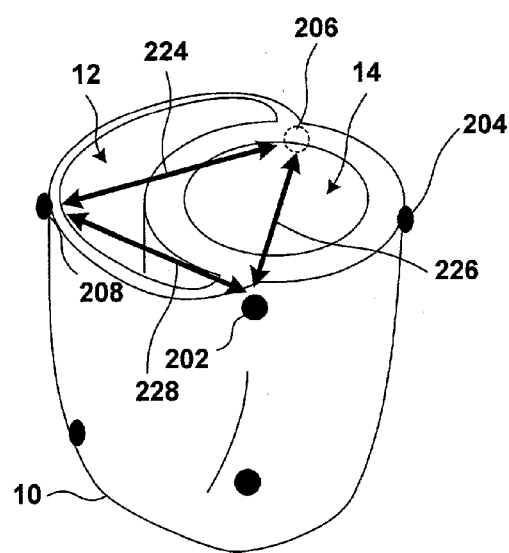
Figure 17:
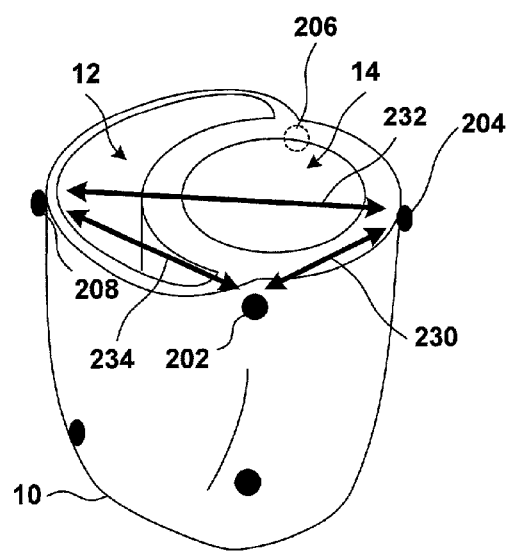

In FIG. 15, impedance 218 can be measured between electrodes 202 and 206, impedance 220 can be measured between electrodes 204 and 206, and impedance 222 can be measured between electrodes 202 and 204. Each of the impedances 218, 220, 222 is a function of the conduction path, with in turn is a function of the volume of left ventricle 14. Similarly, as shown in FIG. 16, impedances 224, 226 and 228, measured among electrodes 202, 206 and 208, are a function of the volume of right electrode 12. As shown in FIG. 17, impedances 230, 232 and 234, measured among electrodes 202, 204 and 208, are a function of the volume of right ventricle 12 and left ventricle 14.

The relationship between impedance and volume for a particular patient may be discovered by experimentation. Changes in impedance, especially decreases in impedance over time, may indicate a reduction in the volume of blood being pumped by the heart, or a reduction of stroke volume. When stroke volume declines, cardiac output generally declines as well. In response to a decline in cardiac output, IMD 84 may pace heart 10 at a higher rate to increase cardiac output. Other strategies for responding to decreases in cardiac output are also possible, such as administration of medicines to increase cardiac contractility.

Impedance measurements shown in FIGS. 15–17 may be made simultaneously, i.e., among several electrodes at once. Alternatively, the impedance measurements may be made sequentially, i.e., impedance measurements may be made between pairs of electrodes in sequence. The invention encompasses impedance measurements made simultaneously, and/or impedance measurements made sequentially.

The invention may offer several advantages, one of which is exceptional versatility. Electrode configurations can be customized to the needs of individual patients. For a patient who needs more electrodes to monitor particular regions of his heart, the invention provides an efficient vehicle for multiple electrode placement at almost any desired locations.

Applications have been described above for customized pacing, cardioversion, defibrillation, cardiac resynchronization and cardiac output monitoring, but the invention is not limited to those applications. The invention has far-reaching applicability to techniques for monitoring and/or therapy that may benefit from multiple electrode placements or electrode placements that may benefit from electrode placements that are customized to the patient.

When used to bring about cardiac resynchronization, the invention's versatility is very valuable. By careful placement of electrodes, the patient's physician can implement interventricular and/or intraventricular cardiac resynchronization therapies that will most benefit the patient. Further, the harness serves to provide support for the heart and helps the heart maintain its shape.

The preceding specific embodiments are illustrative of the practice of the invention. It is to be understood, therefore, that other expedients known to those skilled in the art or disclosed herein may be employed without departing from the invention or the scope of the claims. For example, the invention is not limited to the particular harnesses shown in the figures.

A harness similar to harness 16, for example, may include a mesh-like restraint with lattice members that form a variety of shapes, such as diamonds, triangles, hexagons, circles, or any regular or irregular polygons. Although the exemplary restraint shown in FIG. 2 includes O-rings as attachment sites, the invention is not limited to harnesses having O-rings as attachment sites. The attachment sites may be of any shape. Although harness 16 does not include embedded electrical connections like harness 150, the invention encompasses a mesh-like restraint that includes embedded electrical connections.

Moreover, the invention is not limited to harnesses having lattice members and dedicated attachment sites. In other words, a harness may include lattice members that serve both as structural members and as attachment sites. The harness may be constructed from a restraint of honeycombed irregular hexagons, for example, and the electrode devices may be configured to engage any of the hexagons.

A harness similar to harness 150 may have multiple circumferential attachment members, may have more or fewer than four support members, and may have more or fewer attachment sites than shown in FIG. 7. Electrical connections need not be embedded in the support members or the circumferential attachment member. Instead, one or more separate leads may connect electrodes to IMD 84, as shown in FIG. 5.

Electrical connections may be embedded various embodiments of the invention. Embedded wires may contribute to forming electrical connections, and may also serve as reinforcing members to limit expansion of the harness under tension.

The invention is not limited to any particular placement of electrodes, nor is the invention limited to any particular attachment technique. Although a snap-coupling attachment is easy to use, the invention encompasses all manners by which electrodes are coupled to the harness. As noted above, the invention is not limited to any time of attachment, and electrodes may be attached to the harness before and/or during surgery. These and other embodiments are within the scope of the following claims.

In the claims, means-plus-functions clauses are intended to cover the recited structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The invention claimed is:

1. An implantable medical device comprising:
    a harness that generally conforms to the shape of a heart and configured so that when implanted only cardiac tissue supports said harness;
    a plurality of attachment site structures sized and formed on the harness and shaped to receive and hold a plurality of electrodes, wherein said electrodes comprise discrete circular plate members, wherein the attachment site structures occupy less area than a plurality of open portions of said harness;

a cardiac activity sensing circuit coupled to at least some of said plurality of electrodes, wherein said sensing circuit is adapted to provide mapping of electrical activity of the heart; and a driver circuit adapted to provide cardiac pacing stimuli and impedance measurements, said driver circuit including addressable switches for the plurality of electrodes.

2. The device of claim 1, wherein the harness is formed from a biocompatible material.

3. The device of claim 1, wherein the attachment site structure comprises an O-ring.

4. The device of claim 1, wherein the attachment site structures comprise an electrical receptacle.

5. The device of claim 1, wherein the harness further includes at least two lattice members that expand to a predetermined size and wherein the at least two lattice members are configured so that when implanted only non-stationary tissue supports said at least two lattice members and said harness.

6. The device of claim 5, wherein the at least two lattice members are coupled to one another with at least one attachment site structure.

7. The device of claim 1, further comprising a pulse generator that delivers a pacing pulse to at least a pair of the plurality of electrodes.

8. The device of claim 1, further comprising a high-voltage output circuit that delivers a defibrillation pulse to the at least a pair of the plurality of electrodes.

9. The device of claim 1, wherein the harness comprises a circumferential attachment member that secures the harness to the heart.

10. The device of claim 1, further comprising a tightening apparatus that secures the harness to the heart.

11. The device of claim 1, wherein the harness comprises:
a circumferential attachment member that secures the harness to the heart; and
a support member that constrains the expansion of the heart.

12. The device of claim 1, wherein the harness comprises:
a circumferential attachment member that secures the harness to the heart; and
a mesh-like restraint that constrains the expansion of the heart.

13. The device of claim 1, further comprising an electrical lead embedded in the harness.

14. The device of claim 1, further comprising an indifferent electrode.

15. The device of claim 1, further comprising a reinforcing member that limits the expansion of the harness.

16. An implantable medical device comprising:
a plurality of substantially circular plate-type electrodes;
a implantable harness that includes at least one attachment site structure and configured so that when implanted only cardiac tissue supports said harness; and
a substantially circular electrode body coupled to each of the electrodes, the electrode body defining a mating structure that mates to the at least one attachment site structure, wherein said harness includes a majority of open areas adjacent the at least one attachment site structure;
a cardiac activity sensing circuit coupled to at least some of said plurality of substantially circular plate-type electrodes, wherein said sensing circuit is adapted to provide mapping of electrical activity of the cardiac tissue; and
circuitry means for addressing at least a discrete pair of said electrodes to provide cardiac pacing therapy, cardiac defibrillation therapy, and impedance measurements between said at least a discrete pair of the electrodes.

17. The device of claim 16, wherein the mating structure includes a groove formed in the electrode body.

18. The device of claim 17, wherein the attachment site comprises an O-ring, and wherein the groove is configured to receive the O-ring.

19. The device of claim 16, wherein the attachment site comprises a receptacle and wherein the mating structure is a plug configured to be received by the receptacle.

20. The device of claim 16, further comprising a lead electrically coupled to at least one of the plurality of substantially circular plate-type electrodes.

21. A method comprising:
coupling at least a pair of a plurality of electrodes to at least a pair of attachment site structures of a harness that generally conforms to the shape of a heart wherein the electrodes comprise substantially circular plate type members and the attachment site structures cooperatively mechanically couple to said electrodes;
securing the harness around at least a portion of one ventricle of the heart, wherein the harness is configured so that when implanted only cardiac tissue supports said harness;
sensing cardiac activity via the at least a pair of the plurality of electrodes, wherein said sensing provides mapping of electrical activity of the cardiac tissue; and
selectively addressing said at least a pair of the plurality of electrodes to provide cardiac pacing stimuli, cardiac defibrillation therapy, and impedance measurements therebetween based at least in part upon the mapping of electrical activity of the cardiac tissue.

22. The method of claim 21, wherein the electrode is a pacing electrode.

23. The method of claim 21, wherein the electrode is a defibrillation electrode.

24. The method of claim 21, further comprising electrically coupling the electrode to an implantable medical device.

25. The method of claim 24, wherein the implantable medical device is at least one of a pacemaker, cardioverter, defibrillator and cardiac monitor.

26. A method comprising:
coupling a first electrode to a first attachment site structure on a harness that generally conforms to the shape of a heart, wherein the harness is configured so that when implanted only cardiac tissue supports said harness;
coupling a second electrode to a second attachment site structure on the harness;
securing the harness around at least a portion of one ventricle of the heart;
mapping electrical activity of the cardiac tissue; and
delivering a pacing therapy regimen to the cardiac tissue based at least in part upon the mapped electrical activity of the cardiac tissue,
wherein the first electrode and second electrode are both substantially circular, plate type metallic members and the first attachment site structure and the second attachment site structure are configured to received the substantially circular, plate type metallic members and the cumulative surface area of the metallic members is less than the cumulative surface area of said harness, and wherein the first electrode and the second electrode are adapted to provide cardiac pacing therapy and to perform impedance measurements therebetween.

27. The method of claim 26, wherein securing the harness comprises disposing the first electrode proximate to a first ventricle and the second electrode proximate to a second ventricle.

28. The method of claim 27, wherein the first electrode and the second electrode are defibrillation electrodes.

29. The method of claim 26, further comprising causing an electrical current to flow from the first electrode to the second electrode.

30. The method of claim 26, further comprising causing an electrical current to flow from the first electrode to an indifferent electrode.

31. The method of claim 26, further comprising measuring an impedance between the first electrode and the second electrode.

32. The method of claim 31, further comprising estimating cardiac output as a function of the impedance measurement.

33. A method comprising:
coupling a first electrode to a first attachment site structure on a harness that generally conforms to the shape of a heart and configured so that when implanted only cardiac tissue supports said harness;
coupling a second electrode to a second attachment site structure on the harness;
coupling a third electrode to a third attachment site structure on the harness;
mapping electrical activity of the cardiac tissue via at least a pair of said first, second and third electrodes;
delivering a pacing therapy regimen to the cardiac tissue based at least in part upon the mapped electrical activity of the cardiac tissue; and
securing the harness around at least one ventricle of the heart,
wherein the first electrode and second electrode are both substantially circular, plate type metallic members and the first attachment site structure and the second attachment site structure are configured to received the substantially circular, plate type metallic members and wherein the cumulative surface area of the metallic members is less than the cumulative surface area of said harness, and wherein the first electrode, the second electrode and the third electrode are adapted to provide selective site cardiac pacing therapy and to provide impedance measurements therebetween.

34. The method of claim 33, wherein the securing the harness comprises disposing the first electrode proximate to a first ventricle, the second electrode proximate to a second ventricle and the third electrode proximate to an apex of the heart.

35. The method of claim 33, further comprising:
selecting a current path, the current path comprising the path taken by current flowing from one of the electrodes to another of the electrodes; and
causing an electrical current to flow along the current path.

36. The method of claim 33, further comprising:
selecting a pair of the electrodes; and
measuring an impedance between the pair of electrodes.

37. The method of claim 36, wherein the pair of electrodes is a first pair, the method further comprising:
selecting a second pair of the electrodes, at least one electrode in the second pair being different from the electrodes in the first pair; and
measuring an impedance between the second pair of electrodes.

38. The method of claim 37, further comprising estimating cardiac output as a function of a signal derived from the impedance measurement.

39. An implantable medical device system comprising:
a harness means for mechanically restraining a heart and is configured so that when implanted only non-stationary tissue supports said harness means;
an attachment site structure means sized and formed on the harness means that is shaped to receive and hold an electrode;
at least two electrodes coupled to a respective attachment site structure, wherein the cumulative area of the electrodes is much less than the cumulative area of said harness and said electrodes are controlled to deliver selective site pacing therapy and impedance measurements therebetween; and.
a pace/sense circuit means operatively coupled to the at least two electrodes and adapted for mapping conduction patterns of the non-stationary tissue for delivering a pacing therapy regimen based at least in part upon the mapped conduction patterns.

40. The device of claim 39, further comprising a pulse generator means that delivers a pacing pulse to the electrode.

41. The device of claim 39, further comprising a high-voltage output circuit means that delivers a defibrillation pulse to the electrode.

42. The device of claim 39, further comprising a securing means that secures the harness means to the heart, wherein said securing means is configured so that when implanted only non-stationary tissue supports said securing means.

* * * * *